United States Patent [19]

Gray

[11] Patent Number: 4,757,079
[45] Date of Patent: Jul. 12, 1988

[54] ANTI-HYPERTENSIVE PIPERIDINE COMPOUNDS

[75] Inventor: Allan P. Gray, Rockville, Md.

[73] Assignee: Dynamac Corporaton, Rockville, Md.

[21] Appl. No.: 877,738

[22] Filed: Jun. 24, 1986

[51] Int. Cl.⁴ .............. A61K 31/445; C07D 211/10; C07D 211/12; C07D 211/14
[52] U.S. Cl. .................. 514/319; 514/307; 514/309; 514/310; 514/312; 514/313; 514/314; 514/323; 544/283; 546/139; 546/141; 546/143; 546/153; 546/159; 546/171; 546/176; 546/177; 546/195; 546/198; 546/201; 546/202; 546/205; 546/206; 546/240
[58] Field of Search .......... 546/201, 205, 139, 141, 546/153, 176, 177, 206; 514/319, 323, 307, 314

[56] References Cited

U.S. PATENT DOCUMENTS

| | | | |
|---|---|---|---|
| 2,695,290 | 11/1954 | Finkelstein et al. | 546/201 |
| 3,043,849 | 7/1962 | Szmuszkovicz | 546/201 X |
| 3,218,333 | 11/1965 | Roozemond et al. | 546/201 X |
| 3,238,215 | 3/1966 | Zenitz | 546/201 |
| 3,489,429 | 1/1970 | Herbst | 546/201 X |
| 4,038,273 | 7/1977 | Hauck et al. | 546/205 X |
| 4,246,268 | 1/1981 | Carr | 546/205 X |
| 4,443,462 | 4/1984 | Carr et al. | 546/206 X |
| 4,478,841 | 10/1984 | Audiau et al. | 514/323 |

OTHER PUBLICATIONS

Sugiyama et al.; "Biolumin. Progr., Proc., Kanagawa-Ken, Jap. (1965), pp. 83-87.
C.A., 67:69165h, Sugiyama et al. (1967).

Primary Examiner—Joseph Paul Brust
Attorney, Agent, or Firm—Larson and Taylor

[57] ABSTRACT

Novel compounds of the formula:

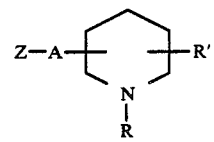

are described wherein Z is a bicyclic aryl group containing between 9 and 10 ring atoms, up to two of which may be nitrogen and up to one of which may be oxygen or sulfur; A is an ethenyl group which may be lower-alkyl-substituted; and R and R' each represent H or an aliphatic group of 1-4 carbon atoms; or a pharmaceutically acceptable acid addition salt thereof.

8 Claims, No Drawings

ANTI-HYPERTENSIVE PIPERIDINE COMPOUNDS

FIELD OF THE INVENTION

The present invention relates to new and therapeutically useful piperidine compounds which have anti-hypertensive properties, and a process for their preparation.

BACKGROUND OF THE INVENTION

It is known that certain piperidine compounds have therapeutic properties. Piperidine derivatives such as those disclosed in U.S. Pat. Nos. 4,443,462 and 4,246,268 have been shown to be useful as tranquilizers and nervous system depressants. A novel group of piperidine compounds have now been discovered which are useful as anti-hypertensive agents.

SUMMARY AND DESCRIPTION OF THE INVENTION

The novel piperidine compounds of the present invention are compounds having the following general structure:

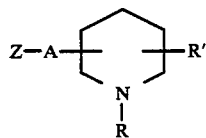

(I)

wherein

Z is a substituted or unsubstituted bicyclic aryl group containing between 9 and 10 ring atoms, up to 2 of which may be nitrogen and up to one of which may be oxygen or sulfur;

A is ethenyl or lower alkyl - substituted ethenyl; and

R and R' each represent H or an aliphatic group of 1–4 carbon atoms;

or a pharmaceutically acceptable acid addition salt thereof.

Illustrative of groups represented by Z are naphthyl, quinolyl, isoquinolyl, quinazolyl, indenyl, indolyl, benzofuranyl, benzothiophenyl, benzothiazolyl. Naphthyl is a preferred bicyclic group. Z may be unsubstituted or substituted by one or more non-interfering groups which do not detract or otherwise interfere with the therapeutic properties of the overall compound. Illustrative of such substitutent groups are halogen, alkyl, alkoxy, nitro, amino and phenyl.

Exemplary of groups represented by R or R' in the compound of the invention are straight and branched chain alkyl groups such as methyl, ethyl, propyl, isopropyl, butyl and isobutyl; hydroxyethyl and the like; and straight and branched-chain alkenyl groups such as allyl, butenyl, isobutenyl and the like.

A specific compound of the invention found to possess extraordinary anti-hypertensive properties is 1-methyl-4-(1-naphthylvinyl)piperidine, which has the formula:

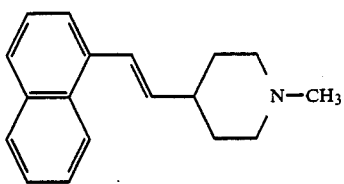

(II)

The compounds of the present invention can be formed into salts by addition of a suitable acid. Pharmaceutically acceptable acid addition salts of these compounds can be organic or inorganic. Illustrative of suitable inorganic acids are hydrochloric, hydrobromic, sulfuric, and phosphoric acids. Examples of suitable organic acids are carboxylic acids, including acetic, propionic, malic, fumaric, and citric, benzoic acid, aminobenzoic acid, and salicylic acid. The preferred compound of the present invention, 1-methyl-4-(1-naphthylvinyl)piperidine has been formed into a hydrochloride salt, and this compound has been designated as B-120.

The compounds of this invention may be prepared by a Wittig reaction wherein a bicyclic arylmethyl-triphenyl-phosphonium is reacted with a piperidine-carbonyl compound, as illustrated below:

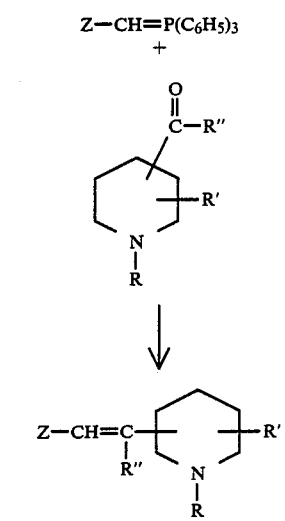

wherein R''=H or a lower alkyl, and Z, R and R' are as previously defined.

Any of the conventional techniques known in the art for effecting the Wittig reaction can be employed to obtain the product of the invention. A preferred procedure involves treating a suspension of a bicyclic arylmethy-triphenyl-phosphonium salt in an inert solvent with a strong base such as n-butyllithium, sodium methoxide or sodium ethoxide and then with a piperidine-carbonyl compound, and stirring the mixture for 16 to 72 hours at a temperature of 20° to 110° C. The precipitate is removed by filtration, washed with ether, and the combined filtrate and ether washings are dried and evaporated to yield the bicyclic arylvinylpiperidine of the present invention.

The preferred compound of the present invention, 1-methyl-4-(1-naphthylvinyl)piperidine, is preferably prepared by a Wittig reaction of 1-naphthyl-triphenyl-phosphonium with 1-methylpiperidine-4-carboxaldehyde.

The pharmaceutical composition of the invention comprises the compound of Formula I or a pharmaceutically acceptable acid addition salt thereof as an active ingredient in an anti-hypertensively effective amount, in combination with a pharmaceutically acceptable carrier for the active ingredient. The preparations can take a form suitable for use in a particular patient. Thus, the pharmaceutical compositions employing the novel compounds may be in solid or liquid form, such as tablets, capsules, powders, solutions, suspensions, etc., and may be administered orally, subcutaneously, intravenously, or intramuscularly. The quantity which comprises an effective amount of the novel compound may be provided in a unit dosage. The nature and quantity of the carrier to be used will vary widely according to the type of pharmaceutical composition employed, and the body weight and tolerance of the particular patient being treated.

Normally the pharmaceutical composition of the invention will be formulated as solid compositions for oral administration. When in solid unit dosage forms, such as tablets or capsules, the compounds can be combined with conventional carriers such as binding agents, including acacia, cornstarch or gelatin, lubricants such as stearic acid or magnesium stearate, or inert fillers which could be lactose, sucrose or corn starch. Injectable solutions for intraveneous or intravascular administration will generally be prepared in physiological saline.

The following examples further illustrate the present invention:

EXAMPLE 1

Preparation of 1-Methylpiperidine-4-carboxaldehyde 4.5 mL(0.06 mole) of formaldehyde solution (37%) was slowly added to a stirred solution of isonipecotic acid (3.88 g, 0.03 mole) in 97% formic acid (6.9 g, 0.15 mole). The mixture was heated to 90°–100° C. A vigorous evolution of carbon dioxide began after 2-3 min. Heat was removed until gas evolution subsided and then the mixture was heated at 95°–100° C. for 8 hours. Aqueous 4N hydrochloric acid (15 mL) was added and the solution was evaporated to dryness. The white syrupy residue was crystallized from isopropyl alcohol to give 1-methylisonipecotic acid hydrochloride as white crystals: mp220°–240°; IR (KBr) 3460, 2960, 2600, 1720, 1465, 1400, 1365, 1300, 1270, 1250, 1205, 1180, 1160, 1040, 980, 955, 920, 875, 830, 720 and 630 $cm^{-1}$; NMR spectrum showed N-CH$_3$ group at $\delta 2.87$.

To a stirred solution of 1-methylisonipecotic acid hydrochloride (178.64 g, 1 mol) in 350 mL of methanol (8 equivalents) was added, dropwise with stirring and cooling (ice-salt bath) to $-10°$ C., 112.8 mL (1.55 equivalents) of thionyl chloride. After completion of the addition (1 hour), the ice-salt bath was removed and the temperature allowed to rise to 40° C. and held at this point for 2 hours. The solution was brought to about pH 8 with sodium carbonate and extracted with methylene chloride. The methylene chloride solution was dried and evaporated to give 136.88 g (87%) of methyl 1-methylpiperidine-4-carboxylate as a clear liquid. The IR spectrum confirmed that the product was the methyl ester.

To a stirred solution of ethyl 1-methylpiperidine-4-carboxylate (3.66 g, 0.0214 mole) in 20 mL of anhydrous ether at $-78°$ under nitrogen gas was added, dropwise, 2 equivalents of diisobutylaluminum hydride (46 mL of a 20% by weight solution in hexane). After the addition (30 min.), the mixture was stirred at $-78°$ for 2 hours. Fifty mL of water was slowly added to decompose the excess hydride. The mixture was stirred at room temperature for one hour. The ether solution was decanted and the aqueous solution was extracted with methylene chloride (3×50 mL). The combined extracts were evaporated in vacuo to give 1-methyl-4-piperidinecarboxaldehyde as a colorless liquid (2.361 g, 86.8%): IR (neat) 2940, 2850, 2790, 2740, 2680, 1725, 1440, 1450, 1380, 1280, 1145, 1090, 1070, 1040, 970, 930 and 760 $cm^{-1}$; NMR (CDCl$_3$) $\delta 1.85$ (m, 5H), 2.05 (m, 2H), 2.22 (s, 3H), 1.65 (m, 2H) and 9.67 (s, 1H). The NMR spectrum clearly indicated the product was the aldehyde (peak at $\delta 9.67$).

Preparation of 1-naphthylmethyltriphenylphosphonium chloride

A mixture of 5.3 g (0.03 mole) of 1-(chloromethyl)-naphthalene and 8.6556 g (0.033 mole) of triphenylphosphine in 150 mL of dimethylformamide was heated at reflux with stirring for 5 hours. A copious white precipitate formed. The precipitate was filtered and washed with 100 mL of dimethylformamide and 100 mL of ether. The product was dried in vacuo to yield 11.97 g (91%) of 1-naphthylmethyltriphenylphosphonium chloride as white crystals: mp 285°–288°; IR (KBr) 3050, 3010, 2880, 2790, 1665, 1590, 1510, 1485, 1440, 1385, 1335, 1275, 1155, 1110, 1095, 875, 810, 785, 730, and 690 $cm^{-1}$; NMR (DMSO) $\delta 5.67$ (d, J=15 Hz, 2H), 7.60 (m, 15H) and 7.73 (m, 7H).

Preparation of 1-methyl-4-(1-naphthylvinyl)piperidine

Next, a 250 mL three-necked round bottomed flask was fitted with a reflux condenser, an addition funnel and a gas inlet tube. A gentle flow of nitrogen was maintained throughout the reaction. To a stirred suspension of 1-naphthylmethyltriphenylphosphonium chloride (4.39 g, 0.01 mole) in 125 mL of anhydrous ether was added, dropwise through a syringe at 0°, an ethereal solution of n-butyllithium (3.85 mL of a 2.6M solution in hexanes). After the addition, the solution was stirred at room temperature for 2 hours as an orange-yellow precipitate formed. A solution of 1-methylpiperidine-4-carboxaldehyde (1.27 g, 0.01 mole) in 25 mL of ether was added dropwise. The reaction mixture became colorless and a white precipitate separated. The mixture was heated under reflux overnight, allowed to cool to room temperature, and the precipitate was removed by filtration. The precipitate was washed with 2×50 mL portions of ether. The combined ethereal filtrates were washed with 3×50 mL portions of water until the washings were neutral. The organic solution was dried (MgSO$_4$) and evaporated in vacuo. The residue was dissolved in petroleum ether and the small amount of triphenyl phosphine oxide ( 0.1 g) that precipitated was removed. The petroleum ether solution was concentrated to give 1-methyl-4-(1-naphthylvinyl)piperidine as a thick syrup. (1.822 g, 73%): IR (KBr) 3060, 3040, 3000, 2940, 2850, 2780, 2740, 2680, 1920 (W), 1800 (W), 1725 (W), 1640 (W), 1590, 1510, 1465, 1445, 1380, 1280, 1200, 1140, 1120, 1070, 970, 850, 780, 720 and 700 $cm^{-1}$; NMR (CDCl$_3$) $\delta 1.70$ (m, 5H), 1.33 (m, 2H), 2.20 (s, 3H), 2.68 (m, 2H), 6.13 (d.d, J=6 Hz, 2H), and 7.40 (m, 7H). The strong absorption at 970 $cm^{-1}$ in the IR spectrum and the NMR peak at $\delta 6.13$ indicated that the major product was the trans-naphthylvinylpiperidine. Gas chromatographic analysis showed that the product contained 87.3% of the trans and 12.7% of the cis isomer.

Ethereal hydrogen chloride was added dropwise to a solution of 1-methyl-4-(1-naphthylvinyl)piperidine in ether at 0° C. to precipitate a yellow solid. The solvent was decanted and the solid was crystallized from ethanol/ether to give white crystals (1.433 g, 69%): mp 195°–197° (dec.); IR (KBr) 3420, 3060, 3010, 2980, 2960, 2920, 2860, 2630, 2560, (br.), 1590, 1510, 1470, 1435, 1400, 1350, 1330, 1270, 1255, 1160, 1045, 1035, 960, 880 and 790 cm$^{31}$ [1]; NMR (DMSO) $\delta$2.02 (br.m, 4H), 2.75 (br.s, 3H), 3.0–3.67 (m, 3H), 3.4 (s, 3H), 5.95–6.47 (m, 2H), and 7.03–8.43 (m, 7H). The NMR spectrum showed that 90% of product was the trans isomer.

EXAMPLE 2

Preparation of 1-Methylpiperidine-4-carboxaldehyde

To a deep cold (below $-70°$ C.) solution of methyl 1-methylisonipecotate (15.7 g. 0.1 mol) in 500 mL of hexane was added, dropwise over 1 hr, 100 mL of 1N diisobutylaluminum hydride (DIBAL-H) in hexane. The solution was stirred for 1.5 h, and 20 mL of saturated aqueous ammonium chloride was very slowly added. The reaction mixture was gradually allowed to come to ambient temperature and stirring was continued for an additional hour. To the reaction mixture was added 10 mL of saturated aqueous sodium bicarbonate and the organic layer was decanted. The aqueous layer was extracted with methylene chloride (200 mL$\times$3) and then with ether (200 mL$\times$3). The combined extracts were dried with magnesium sulfate and evaporated to give 10 g (79%) of a pale yellow oil (crude). The crude aldehyde was used for further reaction without purification.

Preparation of 1-methyl-4-(1-naphthylvinyl)piperidine

To a mixture of the crude aldehyde and 34.5 g (0.079 mol) of 1-naphthylmethyltriphenylphosphonium chloride in 300 mL of ether was added 22.8 mL (0.1 mol) of 25% sodium methoxide solution in methanol. The orange mixture was stirred for 3 days at ambient temperature, and evaporated. The resulting residue was extracted with 800 mL of hexane. The extract was washed with water (100 mL), dried with magnesium sulfate and evaporated to give a pale yellow semisolid. The semisolid was dissolved in 500 mL of ether. Dry hydrogen chloride was bubbled through the ethereal solution to precipitate a white solid. The solid was collected by filtration and recrystallized from ethanol-ether (or isopropyl alcohol-ethyl acetate) to give 8 g (28% from methyl 1-methylisonipecotate) of 1-methyl-4-(1-naphthylvinyl)piperidine hydrochloride (B-120): mp 196°–199° C. NMR d(CD$_3$OC) $\delta$1.75–1.91 (m, 2H), 2.09–2.30 (m, 2H), 2.55–2.70 (br, 1H), 2.91 (s, 3H), 3.00–3.20 (m, 2H), 3.48–3.66 (m, 2H), 6.20 (dd, 1H, J=7 Hz and 16 Hz), 7.28 (d, 1H, J=16 Hz), 7.36–7.61 (m, 4H), 7.73–7.89 (m, 2H), 8.07–8.16 (m, 1H). IR: 2950, 2680, 2550, 1740, 1460, 14410, 1250, 1040, 950 and 780 cm$^{-1}$.

Anal. Calcd for C$_{18}$H$_{22}$NCl.$\frac{1}{2}$ H$_2$O: C, 72.85; H, 7.76; N, 4.72. Found: C, 72.46; H, 7.90; N, 484.

EXAMPLE 3

Pharmacological actions of 1-methyl-4-(1-naphthylvinyl)piperidine hydrochloride (B-120) were evaluated in vitro and in vivo and its efficacy in lowering blood pressure was demonstrated in the cat.

Tested on the guinea pig ileum, B-120 was found to be essentially devoid of anticholinergic activity; on a relative scale it was 5.5$\times$10$^{-4}$ less potent than atropine sulfate.

On a rat hemidiaphragm preparation designed to act essentially as a closed system, B-120 at a concentration of 35 mg/L caused an immediate 2- to 3-fold increase in perfusate volume, indicating a potent vasodilatory effect. Perfusate volume returned to normal after removal of the B-120. At a concentration of 17.5 mg/L, the increase in perfusate volume was not significant and it could be demonstrated that, in the presence of DFP, B-120 completely blocked the release of acetylcholine normally elicited by stimulation of the preparation at 1 Hz. Acetylcholine release returned to normal after removal of the B-120 indicating that the block was reversible.

In the cat, in a dose range of 0.5 to 50 mg/kg (i.v.), B-120 produced a dose-related decrease in both mean blood pressure and heart rate. There appeared to be a greater decrease in diastolic than systolic blood pressure. Representative results are as follows:

| i.v. Dose (mg/kg) | % Control | | |
|---|---|---|---|
| | Mean Blood Pressure | Pulse Pressure | Heart Rate |
| 5.0 | 60 | 110 | 90 |
| 10.0 | 30 | 70 | 80 |
| 50.0 | 0 | 0 | 0 |

At 5 mg/kg mean blood pressure remained down for one to 2 hours and slowly returned to normal. At 50 mg/kg death appeared to be caused by hypotensive crisis since the heart rate did not show evidence of abnormal rhythm.

B-120 at 1 to 10 mg/kg (i.v.) did not alter the response either to vagal stimulation or to exogenous acetylcholine in the cat, confirming the lack of effect of the compound on peripheral muscarinic receptors. In the same dose range, B-120 also did not diminish the responsiveness of the nictitating membrane to either pre- or postganglionic stimulation indicating that the compound does not interfere with neurotransmission at the ganglion. Further, B-120 induced no significant decrease in neuromuscular twitch response in the cat, indicating that the compound had no significant effect on neuromuscular function. Moreover, in cats with sympathetic and parasympathetic neurotransmission completely blocked by pretreatment with hexamethonium and atropine, administration of B-120 still induced a reduction in heart rate and mean blood pressure comparable to that induced in the absence of the blocking agents.

Thus, B-120 produces vasodilation and reduction in heart rate resulting in a reduction in mean blood pressure. The effects are not caused by an action on muscarinic receptors or on the sympathetic nerves innervating the blood vessels. It therefore appears likely that the vascular effects of B-120 may be mediated via direct relaxation of the smooth muscle in the blood vessel walls. The fact that under certain conditions B-120 blocks acetylcholine release at the neuromuscular junction raises the possibility that the postulated relaxation of smooth muscle may involve interference with calcium transport.

I claim:

1. A compound of the formula:

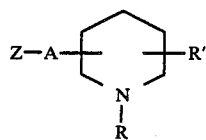

wherein

Z is a bicyclic aryl group selected from naphthyl, quinolyl, isoquinolyl, idenyl and indolyl, which group may be unsubstituted or may bear a substituent selected from halo, alkyl, alkoxy, nitro and amino;

A is an ethenyl group which may be lower alkyl-substituted;

R is selected from H, lower alkyl, lower alkenyl and hydroxyethyl;

R' is H or lower alkyl;

or a pharmaceutically acceptable acid addition salt thereof.

2. A compound of claim 1 wherein Z is naphthyl.

3. A compound of claim 1 wherein A is an ethenyl radical.

4. A compound of claim 1 wherein R is a lower alkyl radical.

5. A compound of claim 4 wherein the lower alkyl radical is methyl.

6. A compound of claim 1 which is 1-methyl-4-(1-naphthylvinyl)piperidine or a pharmaceutically acceptable addition salt thereof.

7. A pharmaceutical composition comprising the compound of claim 1 as an active ingredient or a pharmaceutically acceptable acid addition salt thereof in an anti-hypertensively effective amount, in combination with a pharmaceutically acceptable carrier for the active ingredient.

8. A method of reducing hypertension in a patient, comprising administering to said patient a therapeutically effective amount of the compound of claim 1.

* * * * *